US00PP28545P3

(12) United States Plant Patent
Howell

(10) Patent No.: US PP28,545 P3
(45) Date of Patent: Oct. 24, 2017

(54) APPLE TREE NAMED 'HOWELL TC2'

(50) Latin Name: *Malus domestica*
Varietal Denomination: Howell TC2

(71) Applicant: William Edward Howell, Prosser, WA (US)

(72) Inventor: William Edward Howell, Prosser, WA (US)

( * ) Notice: Subject to any disclaimer, the term of this patent is extended or adjusted under 35 U.S.C. 154(b) by 360 days.

(21) Appl. No.: 14/544,404

(22) Filed: Dec. 31, 2014

(65) Prior Publication Data

US 2015/0195969 P1 Jul. 9, 2015

Related U.S. Application Data

(60) Provisional application No. 61/924,166, filed on Jan. 6, 2014.

(51) Int. Cl.
*A01H 5/08* (2006.01)

(52) U.S. Cl.
USPC ..... Plt./161

(58) Field of Classification Search
USPC ..... Plt./161
CPC ..... A01H 5/0875
See application file for complete search history.

(56) References Cited

PUBLICATIONS http://read.dmtmag.com/i/146156-august-2013/13 (Good Fruit Grower); Aug. 2013; 2 pages.*

* cited by examiner

*Primary Examiner* — Kent L Bell
(74) *Attorney, Agent, or Firm* — Michelle Bos Legal LLC

(57) ABSTRACT

A new and distinct apple tree is disclosed. 'Howell TC2' is notable for its distinctive fruit, which has red skin and red flesh with a sweet/tart flavor.

3 Drawing Sheets

Latin name of the genus and species of the plant claimed: *Malus domestica.*
Variety denomination: 'Howell TC2'.

CROSS-REFERENCE TO RELATED APPLICATIONS

None.

STATEMENT REGARDING FEDERALLY SPONSORED RESEARCH OR DEVELOPMENT

None.

BACKGROUND OF THE INVENTION

The new variety of apple tree 'Howell TC2' was created in the course of a planned breeding program carried out in Prosser, Wash. 'Howell TC2' originated as a result of an open pollination cross in 2001 of 'Airlie Red Flesh' (seed parent, not patented) with the likely pollen parent being 'Honeycrisp' (U.S. Plant Pat. No. 7,197, expired). 'Howell TC2' was selected in 2010 as a single plant from among a population of seedlings derived from the parents, and was selected for its quality of fruit and the red color of the fruit flesh. It is distinguished from its parents by its red skin and red flesh color and by its flavor. Asexual propagation by budding was first carried out in Prosser, Wash. The variety has since been observed over a number of asexually propagated generations, and has been found to remain true to type.

BRIEF SUMMARY OF THE INVENTION

'Howell TC2' is a new and distinct apple tree notable for its distinctive fruit, which has a red flesh and a sweet/tart flavor. A comparison of 'Howell TC2' to related and similar varieties is shown in Table 1 below.

TABLE 1

Comparison of 'Howell TC2' to Related and Similar varieties

| | 'Airlie's Red Flesh' | 'Honeycrisp' | 'Howell TC2' | 'Howell TC3'* |
|---|---|---|---|---|
| Bloom Color | Dark pink | White | Pink | Light pink |
| Bloom Timing | −2 days | 0 | +3 days | −1 day |
| Flesh Color | Pink | Pink | Red | Red |
| Skin Color | Light green | Red and green | Red | Yellow |
| Lenticel Color | White | White | White | Light yellow |
| Lenticels/in$^2$ | 15 to 25 | 15 to 25 | 10 to 20 | 15 to 20 |
| Fruit Maturity | +3 days | 0 | +7 days | +4 days |
| Fruit flavor | Crunchy, sweet | Crisp, very juicy, sweet-tart | Crisp, juicy, sweet-tart with berry notes | Crisp, juicy, sweet-tart with berry notes |
| Tree Vigor | Moderate | Non-vigorous | Non-vigorous | Moderate |
| Fruit in common storage | Okay for 2 months | Stores well for 4 months | Stores well for 4 months | Stores well for 4 months |

*'Howell TC3' - U.S. Plant Pat. pending, Ser. No. 14/544,402

BRIEF DESCRIPTION OF THE PHOTOGRAPHS

Figure 1:
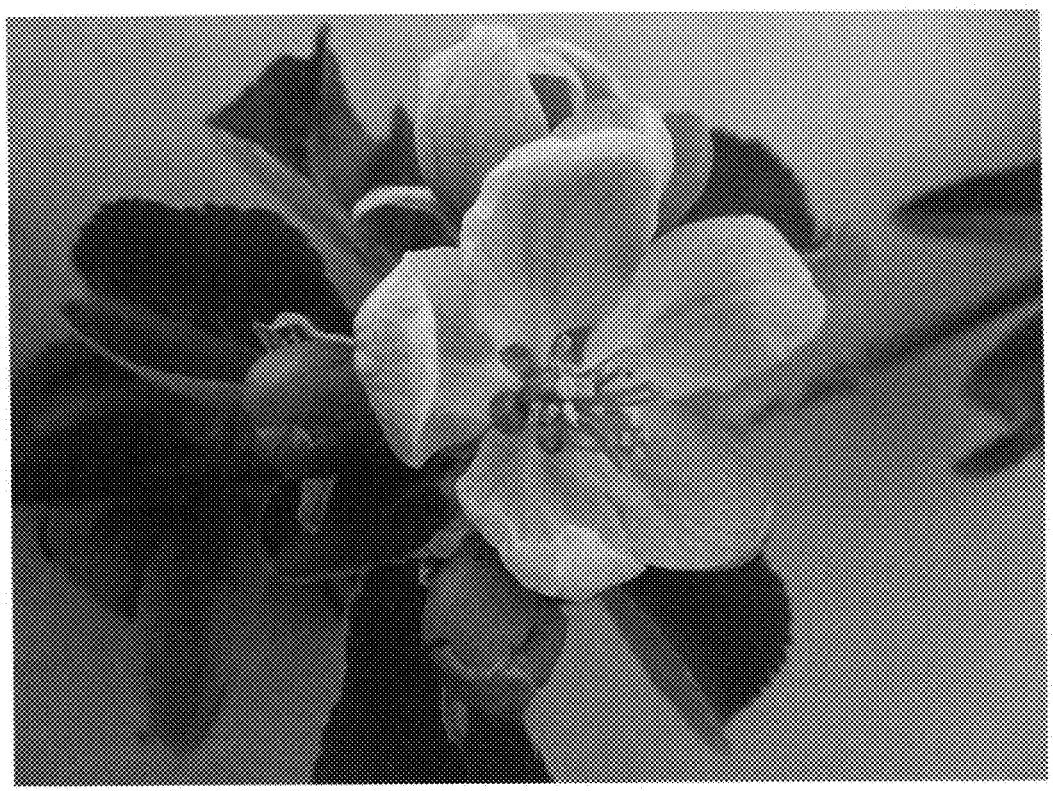
Figure 2:
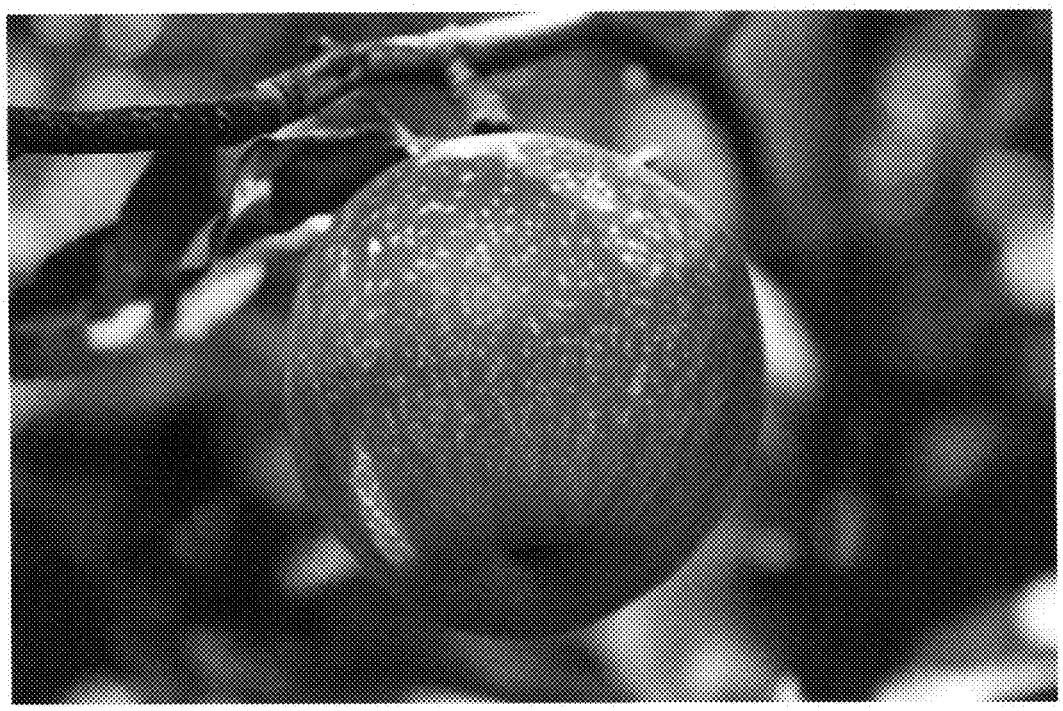

FIG. 1 shows the blossom from the tree of the new cultivar;

FIG. 2 the fruit of the new cultivar on the tree; and

Figure 3:
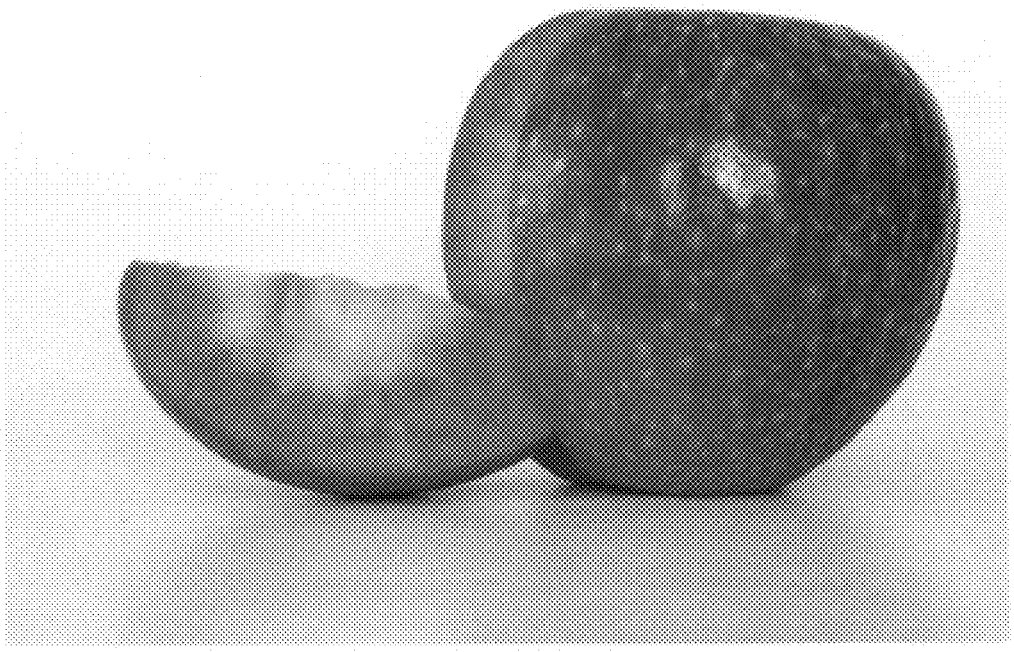

FIG. 3 shows the flesh of the fruit of the new cultivar.

DETAILED BOTANICAL DESCRIPTION

The following detailed botanical description is based on observations made during the 2013 and 2017 growing seasons at Prosser and Wapato, Wash. All colors are described according to The Royal Horticultural Society Colour Chart as published in 2001. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:
- *Vigor*.—Low to moderate.
- *Size*.—Height 9.5 feet; Spread 4 feet.
- *Trunk*.—Diameter at 30 cm above graft union 2.54 cm.
- *Bark texture*.—Smooth.
- *Bark coloration*.—Gray-brown N199D.
- *Lenticels*.—Rectangular, length 2 mm, white 155D, density 12/in$^2$.

Branch:
- *Size*.—Length 30.48 cm; Diameter 0.95 cm at 1 m above ground.
- *Crotch angle relative to trunk*.—70°.
- *Color*.—Gray-brown N199D.
- *Lenticels*.—Round, length 1 mm, white 155D, density 16/in$^2$.

Dormant one-year-old shoot:
- *Size*.—Diameter 0.95 cm, length 71.1 cm.
- *Color*.—Greyed-orange 177A.
- *Internode length*.—2.54 cm.
- *Lenticels*.—Round, length 0.5 mm, white 155D, density 20/in$^2$.

Flowers:
- *Bud shape*.—Tapered cylinder.
- *Bud length*.—0.64 cm.
- *Bud diameter*.—0.48 cm.
- *Color of closed bud*.—Red-purple 58A.
- *Color at balloon stage*.—Red-purple N57C.
- *Diameter of open flower*.—3.81 cm.
- *Petal*.—Quantity per flower 5.
- *Margin*.—Smooth.
- *Relative position of petal margin*.—Overlapping.
- *Petal shape*.—Obovate with rounded apex, cuneate base.
- *Petal length*.—2.54 cm.
- *Petal width*.—1.91 cm.
- *Color of upper surface*.—Red-purple N57D.
- *Color of lower surface*.—Red-purple N57D with stripe of red-purple 58A.
- *Pistil length*.—11 mm.
- *Pistil color*.—Yellow 1D.
- *Anther quantity*.—18 to 25.
- *Anther length*.—0.32 cm.
- *Color of pollen*.—Yellow 2C.
- *Stigma length*.—0.16 cm.
- *Stigma color*.—Yellow 1D.
- *Style length*.—1.9 cm.
- *Style color*.—Yellow 1D.
- *Ovary size*.—Length 5 mm, diameter 3 mm.
- *Ovary color*.—Yellow-green 146B.
- *Bloom period*.—First bloom April 23, full bloom May 2 in Prosser, Wash.

Pedicel:
- *Length*.—1.9 cm.
- *Diameter*.—0.16 cm.
- *Color*.—Yellow-green 145C.

Sepals:
- *Quantity*.—5.
- *Color*.—Upper surface yellow-green 148D, lower surface yellow-green 144D.
- *Length*.—15 mm.
- *Width*.—4 mm.
- *Shape*.—Lanceolate with pointed apex.
- *Margin*.—Smooth.

Leaf:
- *Shape*.—Ovate.
- *Texture*.—Upper surface smooth, lower surface veined.
- *Venation*.—Pinnate.
- *Attitude in relation to shoot*.—Nearly horizontal.
- *Blade margin*.—Serrated.
- *Apex*.—Acute.
- *Base shape*.—Rounded.
- *Size*.—Length 10.2 cm, width 5.7 cm.
- *Color of upper surface*.—Yellow-green 146A.
- *Color of lower surface*.—Yellow-green 146D.

Petiole:
- *Length*.—3.2 cm.
- *Diameter*.—0.16 cm.
- *Color*.—Red-purple 64C.

Stipules:
- *Quantity*.—2.
- *Shape*.—Lanceolate.
- *Length*.—5 mm.
- *Width*.—0.5 mm.
- *Color*.—Upper surface yellow-green 147D, lower surface yellow-green 148D.

Fruit:
- *Size*.—Diameter 7.4 cm, height 7.4 cm.
- *Weight*.—180 g.
- *General shape in profile*.—Rounded; Ribbing absent.
- *Crowning at calyx end*.—Slight.
- *Eye basin*.—Depth 4 mm, width 15 mm.
- *Stalk*.—Length 1.9 cm, width 0.16 cm, color yellow-green 145B; Depth of stalk cavity 1.27 cm; Width of stalk cavity 0.64 cm.
- *Size of lenticels*.—0.16 cm.
- *Color of lenticels*.—White 155A.
- *Ground color of skin*.—Yellow 4C.
- *Over color of skin*.—Red 46B.
- *Amount of over color on skin*.—90%.
- *Pattern of over color*.—Blush; Flesh is crisp and very juicy.
- *Flesh color*.—Red 50B with white 155B (See FIG. 3).
- *Brix*.—15°.
- *Aroma*.—Faint.
- *Quantity of seeds*.—7-10.
- *Shape of seed*.—Acuminate.
- *Seed size*.—Length 10 mm, width 5 mm.
- *Seed color*.—Greyed-orange 166A.
- *Locules*.—5 per fruit, length 15 mm, width 7 mm.
- *Number of fruit per cluster*.—4 to 5.

Harvest: About 7 days after 'Honeycrisp'.

Eating quality: Crisp, juicy, sweet-tart with berry notes.

Storage characteristics: Stores well in common storage for 4 months.

Winter hardiness: Hardy in areas tested (Prosser and Wapato, Wash.).

Disease resistance/susceptibility: None noted.

Use: Fresh Market and processing.

The invention claimed is:

1. A new and distinct Apple tree as illustrated and described.

* * * * *